(12) United States Patent
Ewing et al.

(10) Patent No.: US 10,325,073 B1
(45) Date of Patent: Jun. 18, 2019

(54) METHOD AND SYSTEM FOR PATIENT ADHERENCE TRACKING

(71) Applicant: WALGREEN CO., Deerfield, IL (US)

(72) Inventors: Susan C. Ewing, Libertyville, IL (US); Kristi Rudkin, Spring Grove, IL (US); Marianna L. Vranicar, Deerfield, IL (US); Michael Taitel, Deerfield, IL (US); Jenny Jiang, Palatine, IL (US); Randy Wolf, Antioch, IL (US); John Mazzaferri, Mount Prospect, IL (US); Koteswar Kothapalli, Buffalo Grove, IL (US); Robert Van Oost, Elgin, IL (US); Richard Frank, Buffalo Grove, IL (US)

(73) Assignee: WALGREEN CO., Deerfield, IL (US)

( * ) Notice: Subject to any disclaimer, the term of this patent is extended or adjusted under 35 U.S.C. 154(b) by 744 days.

(21) Appl. No.: 14/487,157

(22) Filed: Sep. 16, 2014

(51) Int. Cl.
*G06F 19/00* (2018.01)

(52) U.S. Cl.
CPC .................... *G06F 19/3456* (2013.01)

(58) Field of Classification Search
USPC ........................................................ 705/2–3
See application file for complete search history.

(56) References Cited

U.S. PATENT DOCUMENTS

| | | | | |
|---|---|---|---|---|
| 8,589,186 B1 * | 11/2013 | Nadas | ................ | G06F 19/3456 705/3 |
| 2013/0090937 A1 * | 4/2013 | Wright | .................... | G06F 19/00 705/2 |
| 2013/0311205 A1 * | 11/2013 | Creswell | ............. | G06F 19/3475 705/3 |

* cited by examiner

*Primary Examiner* — Michael Tomaszewski
(74) *Attorney, Agent, or Firm* — Marshall, Gerstein & Borun LLP; Randall G. Rueth

(57) ABSTRACT

The method and system determine and report measures of adherence of patients to prescription medication regimens based upon fill gaps in the prescription history of the patients. The measure of adherence may be the proportion of days covered by the medication. The method and system may receive or access information relating to a patient's medical history, including past prescription medication fills. Fills of both the prescription medication and other medications that may substitute for the prescription medication may be considered in determining patient adherence levels. Upon determining the patient's level of adherence, the system and method may generate a report including the adherence information and associated information, such as a home pharmacy location. The report may include an indication of whether new-to-therapy information should be presented to a patient based on patient adherence levels.

18 Claims, 6 Drawing Sheets

METHOD AND SYSTEM FOR PATIENT ADHERENCE TRACKING

TECHNICAL FIELD

The present disclosure generally relates to a system and a method for determining and reporting adherence levels of patients to prescription medication regimens.

BACKGROUND

Effective management of a patient's medication therapy is an important factor in achieving successful treatment results. The more closely a patient adheres to his or her prescribed medication treatment regimen, the more likely it is that the treatment will be effective. Unfortunately, in many instances patients do not adequately comply with their medication therapy regimens. Poor compliance with treatment regimens can result in negative health impacts for the patient as well as negative impacts on those who have an interest in maintaining the patient's health.

For many patients with chronic medical conditions, the key to successful treatment of their conditions is adherence to a doctor-prescribed regimen of prescription medications. However, the regimen often consists largely of taking medication every day (or multiple times per day) at home or wherever the patient may be. Additionally, as patients age, it is common for each patient to develop multiple chronic diseases. For example, an elderly man might be undergoing treatment for high blood pressure, diabetes, and prevention of a second heart attack. Thus, his treatment plan might require him to self-administer several drugs at different times of the day and get prescriptions filled on time. Often, regimen instructions are confusing, or the drugs cause unforeseen or uncomfortable side-effects. In other cases, the patient may have a history of non-compliance with his or her treatment regimen, based on any number of causes, such as difficulty in filling prescriptions, lack of adequate instruction, forgetfulness, etc. In any event, failure to comply with instructions or a prescription medication regimen may cause a preventable hospital admission or doctor visit. Failure to comply may also cause a doctor to change unnecessarily (or, conversely, not to change when necessary) the regimen based on insufficient or inaccurate information about a patient's compliance with the regimen. Whether the patient follows post-discharge instructions and appropriately uses the medications prescribed is largely unregulated by any healthcare provider, healthcare facility, or pharmacist.

SUMMARY

A method, system, and computer-readable medium storing instructions for tracking adherence of a patient to a treatment regimen including a prescription medication are disclosed herein. One embodiment comprises a computer-implemented method including receiving information regarding a prescription history of the patient, determining one or more fill gaps between any of the first instance and the one or more subsequent instances based upon the prescription history, calculating a measure of adherence of the patient to the treatment regimen based on the one or more fill gaps, generating a report based at least in part upon the calculated measure of adherence, and presenting the report to a user. The prescription history may include a first instance in which the patient has received the prescription medication and one or more subsequent instances in which the patient has received the prescription medication following the first instance. Each instance may be a fill or refill of a prescription for the prescription medication, and the fills or refills may relate to the same prescription or multiple prescriptions for the prescription medication. The fill gaps may be periods of time during which the patient had an insufficient supply of the prescription medication for to the treatment regimen.

In one embodiment, the method, system, and computer-readable medium may further receive an indication of a new prescription to fill for the patient and determine whether to include an instruction to provide new-to-therapy information to the patient in the report based upon the prescription history of the patient and the measure of adherence of the patient to the treatment regimen including the prescription medication. The new prescription may relate to a second prescription medication, and the new-to-therapy information may include information regarding the second prescription medication and information regarding proper usage. Determining whether to include the instruction in the report may be based upon information regarding the prescription medication, including at least one adherence metric for a plurality of patients and relating to one or more of the following: the prescription medication, a dosage of the prescription medicine, a therapeutic class including the prescription medication, a pharmacy location associated with the new prescription fill, a home pharmacy location associated with the patient, or demographic information regarding the patient.

In additional embodiments, the method, system, and computer-readable medium may further determine a home pharmacy location associated with the patient. The home pharmacy location may be one of a plurality of pharmacy locations at which the patient has received a fill of one or more prescription medications. The home pharmacy location may also be determined at least in part based upon one or more of the following: a mailing address of the patient, a telephone number of the patient, an insurance policy provider of the patient, a customer account of the patient, or the prescription history of the patient.

In some embodiments, the generated report may include information regarding the patient and a plurality of additional patients associated with the home pharmacy location. Additionally, or alternatively, the report may include information regarding one or more purchases associated with the patient at one or more locations, which purchases may include one or more non-prescription medical products. The report may further include an instruction to hold a consultation with the patient based upon the one or more purchases of the patient and information regarding the treatment regimen.

In some embodiments, the prescription history may include one or more of the first instance or subsequent instances in which the patient has received a second prescription medication in the same therapeutic class as the prescription medication. In such embodiments, each fill gap may be a period of time during which the patient had an insufficient supply of either the prescription medication or the second prescription medication according to the treatment regimen. Additionally, or alternatively, the measure of adherence may be a measure of the proportion of days covered (PDC), comprising a proportion of a number of days in a measurement period for which the patient had a sufficient supply of the prescription medication according to the treatment regimen to a number of days in the measurement period. The measure of adherence may also be a measure of a medication possession ratio (MPR), comprising the a ratio of a measure of days supplied by a cumulative total of all instances in which the patient received the prescription medication during the measurement period according to the treatment regimen to the number of days in the measurement period. The measurement period may be the shorter of (i) a period between the first instance and an end date for determining the measure of adherence and (ii) a period of predetermined length immediately preceding the end date for determining the measure of adherence.

Another embodiment comprises a computer system including one or more processors, one or more databases, and a tangible program memory storing executable instructions that, when executed by the one or more processors, cause the computer system to receive information regarding a prescription history of the patient, determine one or more fill gaps between any of the first instance and the one or more subsequent instances based upon the prescription history, calculate a measure of adherence of the patient to the treatment regimen based on the one or more fill gaps, and generate a report based at least in part upon the calculated measure of adherence. Another embodiment comprises a tangible, non-transitory computer-readable medium storing instructions that, when executed by at least one processor of a computer system, cause the computer system to receive information regarding a prescription history of the patient, determine one or more fill gaps between any of the first instance and the one or more subsequent instances based upon the prescription history, calculate a measure of adherence of the patient to the treatment regimen based on the one or more fill gaps, and generate a report based at least in part upon the calculated measure of adherence.

BRIEF DESCRIPTION OF THE DRAWINGS

The figures described below depict various aspects of the applications, methods, and systems disclosed herein. It should be understood that each figure depicts an embodiment of a particular aspect of the disclosed applications, systems and methods, and that each of the figures is intended to accord with a possible embodiment thereof. Furthermore, wherever possible, the following description refers to the reference numerals included in the following figures, in which features depicted in multiple figures are designated with consistent reference numerals.

DETAILED DESCRIPTION

Figure 1A:
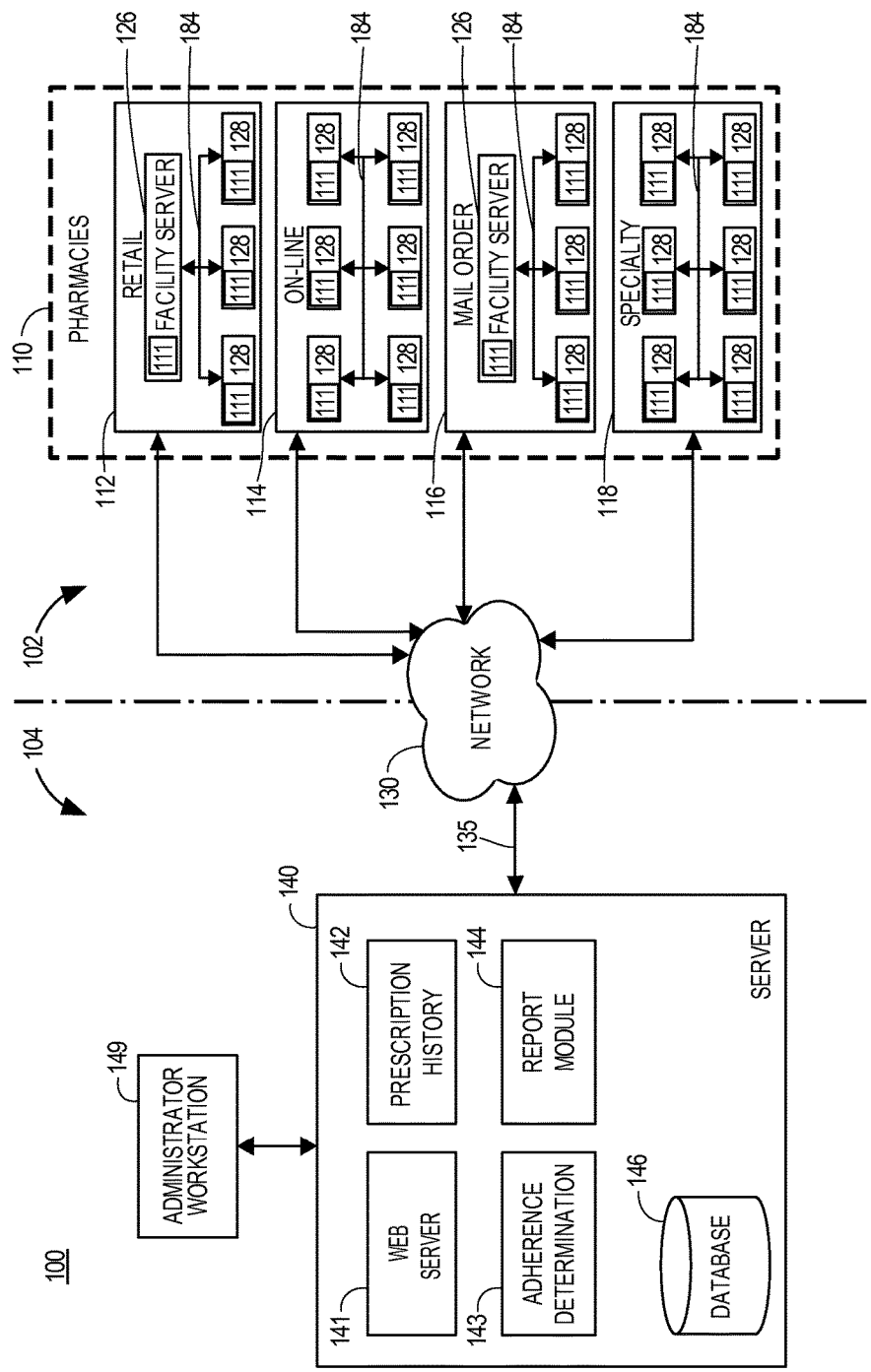
FIGS. 1A-1C illustrate block diagrams of a computer network, a computer server, and computing terminals on which an exemplary adherence tracking system may operate in accordance with the described embodiments.

Although the following text sets forth a detailed description of numerous different embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

As used herein, the term "patient" means the person named on a prescription for a prescription medication. As used herein, the term "interested third party" means any individual, organization, program, or entity, other than a patient or a pharmacy, that requests that an adherence report be generated, information regarding patient adherence levels that may be obtained from an adherence report, or an action based upon patient adherence information (e.g., requests pharmacies hold consultations with non-adherent patients meeting some predetermined criteria). Interested third parties may include third-party payors, pharmaceutical manufacturers, medical health plans, medical care providers, health systems, governmental agencies, private organizations, or researchers.

Also, as used herein, the term "pharmacy" means retail drug stores, as well as any other channels through which prescription medications are dispensed to patients, such as an on line pharmacy, a mail order pharmacy, or a specialty pharmacy. Whichever channel the patient chooses, the patient or someone acting on the patient's behalf must typically interact with a pharmacist or other pharmacy staff to have a prescription filled. Generally, a prescription has associated with it a plurality of data. The data may include, but is not limited to: a date the prescription was written; a doctor who prescribed the medication; a name of the medication prescribed; an indication of whether a generic may be substituted for the prescribed medication; a number of days of medication to be filled; a number of fills prescribed; a first date on which the prescription was filled (referred to herein as the "first fill date"); one or more dates on which the prescription was refilled (referred to herein as "refill dates"); a date on which the prescription was most recently filled (referred to herein as the "last fill date"); and a pharmacy at which it was most recently filled. A patient profile may be created for every patient who fills a prescription at a pharmacy to store important information about the patient and the various pharmacy or non-pharmacy services that have been provided to the patient. The patient profile may include basic patient information, such as name, address, phone number, insurance group number, prescription history, etc. The prescription history may include, but is not limited to, data such as: a list of the patient's prescriptions, and for each, the first fill date, one or more fill dates, one or more fill locations, the last fill date, a number of fills remaining, or other information related to the patient's prescriptions. In some embodiments, the patient profile may include information relating to customer loyalty programs, non-prescription medicine purchases, non-medical purchases, participation in third-party wellness programs, or other information regarding the patient.

FIG. 1A illustrates a block diagram of an exemplary adherence tracking system 100 for tracking and reporting patient adherence to a prescription medication regimen, as described in FIGS. 2-4 below. The high-level architecture includes both hardware and software applications, as well as various data communications channels for communicating data between the various hardware and software components. The adherence tracking system 100 may be roughly divided into front-end components 102 and back-end components 104. The front-end components 102 may be disposed within one or more pharmacies 110. Where there is more than one pharmacy 110, the pharmacies 110 may be located, by way of example rather than limitation, in separate geographic locations from each other, including different areas of the same city or different states. The front-end components 102 may comprise a plurality of pharmacy workstations 128. The pharmacy workstations 128 may be local computers located in the various pharmacies 110 that execute a variety of applications related to pharmacy management. Pharmacists, technicians, or other users (not shown) may use the pharmacy workstations 128 to access patient information, enter new prescriptions, access insurance and payment information, and perform other pharmacy management-related tasks. Thus, the front-end components 102 may include pharmacy workstations 128 for servicing patients visiting an in-store retail pharmacy 112, pharmacy workstations 128 for servicing patients who choose to fill their prescriptions through an on-line pharmacy 114, a plurality of pharmacy workstations 128 for servicing patients who prefer to use the services of a mail-order pharmacy 116, and a plurality of pharmacy workstations 128 for servicing patients who require the services of a specialty pharmacy 118.

Those of ordinary skill in the art will recognize that the front-end components 102 could also comprise a plurality of facility servers 126 disposed at the pharmacies 110, instead of or in addition to a plurality of pharmacy workstations 128. Each pharmacy 112, 114, 116, 118 may include one or more facility servers 126 that may be utilized to facilitate communications between the pharmacy workstations 128 and the back-end components 104 via a network 130, described below, and to store information for a plurality of patients, employees, accounts, or other records associated with each facility. Further, each pharmacy 112, 114, 116, 118 may include one or more pharmacy workstations 128 operatively connected to the facility server 126 via a local network 184.

The front-end components 102 may communicate with the back-end components 104 via the network 130. The network 130 may be a proprietary network, a secure public internet, a virtual private network or some other type of network, such as dedicated access lines, plain ordinary telephone lines, satellite links, cellular data networks, combinations of these, etc. Where the network 130 comprises the Internet, data communications may take place over the network 130 via an Internet communication protocol. The back-end components 104 include one or more servers 140. Each server 140 may include one or more computer processors adapted and configured to execute various software applications and components of the adherence tracking system 100, in addition to other software applications. The server 140 may further include a database 146 that is adapted to store data related to the prescription medication histories of a plurality of patients. Such data may include, for each of a plurality of patients, information regarding one or more original or refill purchases of one or more prescription medications (e.g., first fill dates, refill dates, and last fill dates). The server 140 may access data stored in the database 146, as well as data stored in other systems (not shown) when executing various functions and tasks associated with the operation of the adherence tracking system 100.

Although the adherence tracking system 100 is shown to include one server 140 and four pharmacies 112, 114, 116, and 118, it should be understood that different numbers may be utilized. For example, the system 100 may include a plurality of servers 140 and hundreds of pharmacies 110, all of which may be interconnected via the network 130. Furthermore, the database storage or processing performed by the one or more servers 140 may be distributed among a plurality of servers 140 in an arrangement known as "cloud computing." This configuration may provide various advantages, such as enabling near real-time uploads and downloads of information as well as periodic uploads and downloads of information. This may in turn support a thin-client embodiment of the pharmacy workstations 128, wherein most of the processing and storage is performed by the servers 140.

Figure 1B:
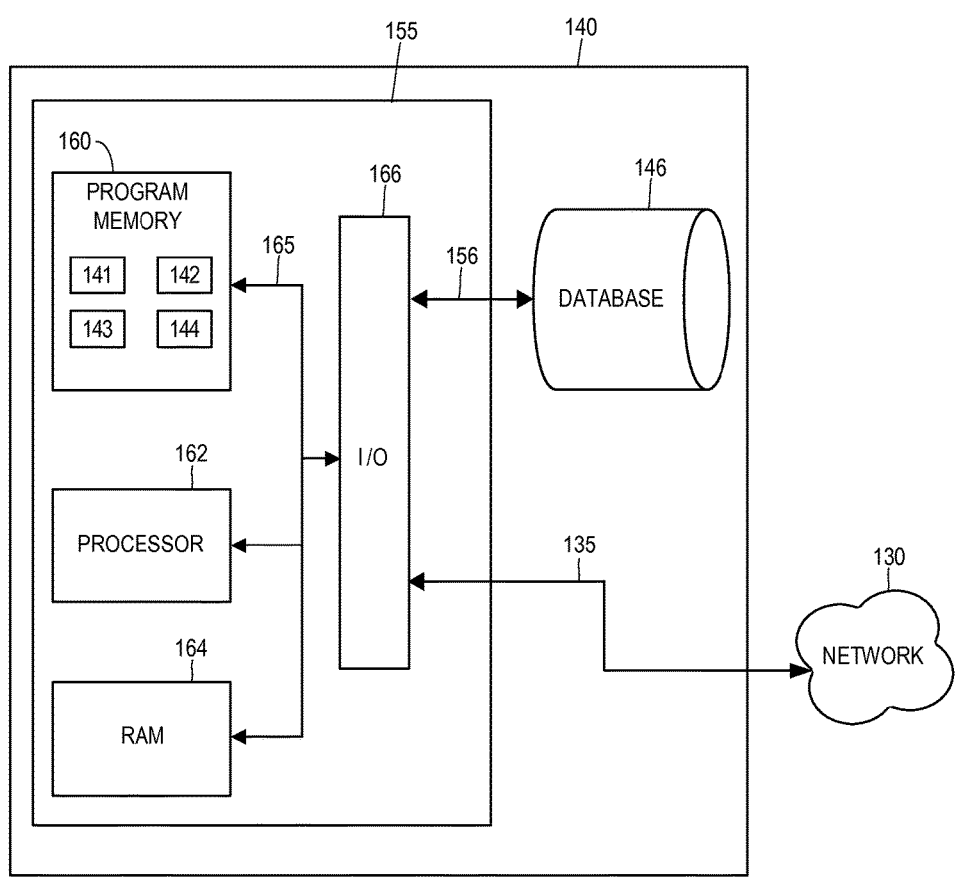

FIG. 1B is a schematic diagram of one possible embodiment of the server 140. The server 140 may have a controller 155 that is operatively connected to the database 146 via a link 156. It should be noted that, while not shown, additional databases may be linked to the controller 155 in a known manner. The controller 155 may include a program memory 160, a processor 162 (which may be called a microcontroller or a microprocessor), a random-access memory (RAM) 164, and an input/output (I/O) circuit 166, all of which may be interconnected via an address/data bus 165. It should be appreciated that although only one microprocessor 162 is shown, the controller 155 may include multiple microprocessors 162. Similarly, the memory of the controller 155 may include multiple RAMs 164 and multiple program memories 160. Although the I/O circuit 166 is shown as a single block, it should be appreciated that the I/O circuit 166 may include a number of different types of I/O circuits. The RAM 164 and program memories 160 may be implemented as semiconductor memories, magnetically readable memories, or optically readable memories, for example. The controller 155 may also be operatively connected to the network 130 via a link 135.

Figure 1C:
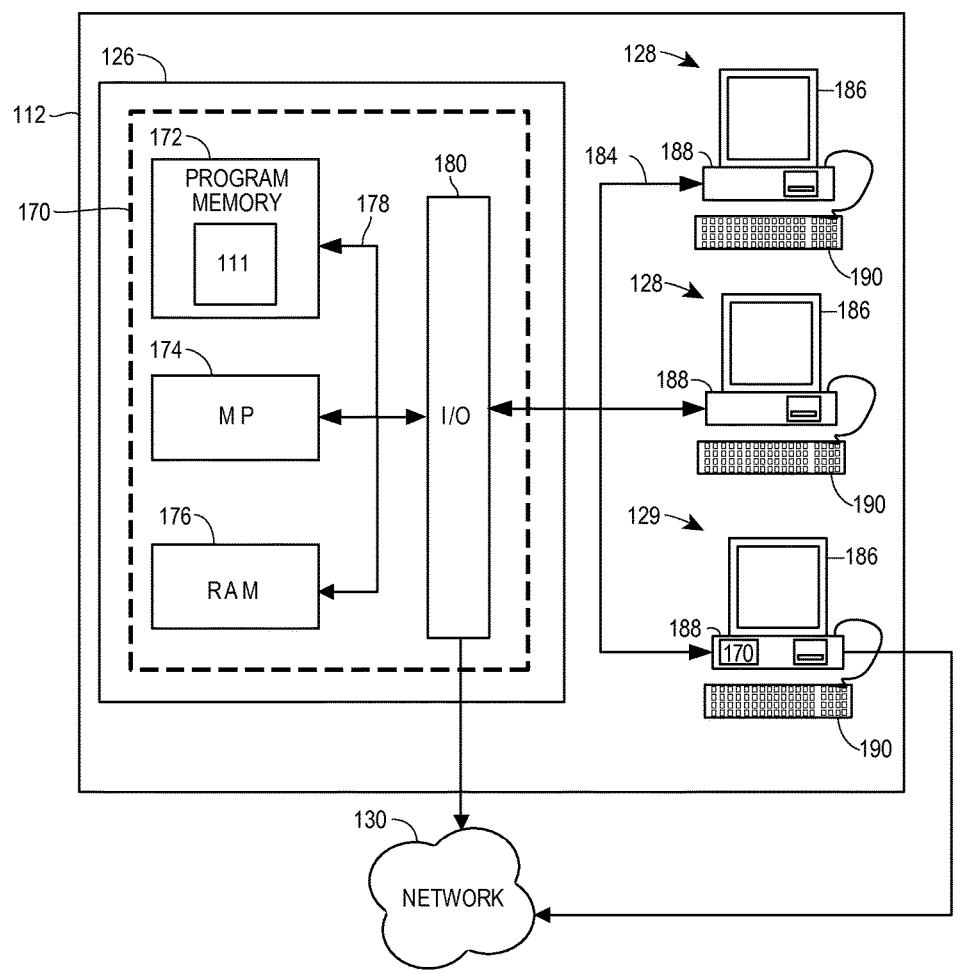

FIG. 1C is a schematic diagram of one possible embodiment of the front-end components 102 located in one or more of the pharmacies 110 from FIG. 1A. Although the following description addresses the design of the pharmacies 110, it should be understood that the design of one or more of the pharmacies 110 may be different than the design of other pharmacies 110. Also, each of the pharmacies 110 may have various different structures and methods of operation. It should also be understood that the embodiment shown in FIG. 1C illustrates some of the components and data connections present in a pharmacy, however it does not illustrate all of the data connections present in a typical pharmacy. For exemplary purposes, one design of a pharmacy is described below, but it should be understood that numerous other designs may be utilized.

Each pharmacy 110 may have one or more pharmacy workstations 128 or one or more facility servers 126. The facility server 126 may be operatively connected to a plurality of pharmacy workstations 128 via a network 184. The network 184 may be a wide area network (WAN), a local area network (LAN), or any other type of network readily known to those persons skilled in the art. The facility server 126 or workstations 128 may also be operatively connected to the server 140 via the network 130.

Each workstation 128 or facility server 126 includes a controller 170. Similar to the controller 155 from FIG. 1B, the controller 170 may include a program memory 172, a microcontroller or a microprocessor (MP) 174, a random-access memory (RAM) 176, and an input/output (I/O) circuit 180, all of which may be interconnected via an address/data bus 178. As discussed with reference to the controller 155, it should be appreciated that although only one microprocessor 174 is shown, the controller 170 may include multiple microprocessors 174. Similarly, the memory of the controller 170 may include multiple RAMs 176 and multiple program memories 172. Although the I/O circuit 180 is shown as a single block, the I/O circuit 180 may include a number of different types of I/O circuits. The RAM 176 and programs memories 172 may also be implemented as semiconductor memories, magnetically readable memories, and/or optically readable memories, for example. In some embodiments, the RAM 176 and program memories 172 may be combined into one memory without materially altering the system 100 as described herein.

The workstations 128 may further include displays 186 and keyboards 190, as well as a variety of other input/output devices (not shown) such as scanners, printers, touch screens, track pads, track balls, voice recognition systems, digital cameras, etc. Pharmacists, technicians, or other users (not shown) may sign on to the pharmacy workstations 128 using any generically available technique, such as entering a user name and password. If users are required to sign on to the pharmacy workstations 128, this information may be passed via the link 184 to the facility server 126, so that the controller 170 will be able to identify which users are signed on to the system. This may be useful in monitoring user productivity.

In one embodiment, the adherence tracking system 100 may utilize a web interface to enable communication between the pharmacies 110 and the server 140, in which case the server 140 may include a web server 141. Those of ordinary skill in the art will appreciate that the web server 141 may be a stand-alone server, or a software module implemented within the server 140. The various front-end components 102 may include a web browser client application 111 to communicate with the back-end components 104. A web server 141 may transmit web pages to the facility servers 126 and pharmacy workstations 128 in response to URL requests received by the web server 141 from the front-end equipment 102 over the network 130. The web pages sent to the front-end equipment 102 may include data in the database 146. It should be noted that, while the current embodiment describes a web server 141 and a web browser client 111, each implementing the hyper-text transfer protocol, the web server 141 could implement any known or later-developed protocol compatible with the web browser client application 111 running on the front-end equipment 102 and adapted to the purpose of receiving and providing the necessary patient information via the network 130.

The server 140 may further include a number of software applications stored in a program memory 160. The software applications may be executed on the same computer processor as the web server application 141, or on different processors. The various software applications may include a prescription history module 142 for accessing information regarding the medical history of a patient, including medicines prescribed and prescriptions dispensed. The prescription history module 142 may request or receive data from the database 146 or other sources of information regarding the patient (not shown). Such other sources may include third-party databases of information regarding the medical histories of patients, including data regarding prescriptions filled at pharmacies (not shown) other than the pharmacies 110. Such other sources may further include databases of general demographic information concerning the patient, the pharmacy 110, or one or more third-party payors or other interested third parties. If part or all of the information is stored in a legacy data system (not shown), the prescription history module 142 may access the legacy data system (not shown) to obtain information regarding the patient, the patient's prescription medication and other medical history, or other relevant information. The software applications may further include an adherence determination module 143 for determining whether a patient is adherent to a prescription medication and a report module 144 for generating a report based upon the prescription history and adherence determination. Those of ordinary skill in the art will appreciate that these modules may be implemented in any number of modules; their functions need not be divided as indicated in FIG. 1A.

Finally, the back-end components 104 may include one or more administrator workstations 149. The administrator workstation 149 allows an authorized user to access the various applications running on the server 140 to alter or adjust the operation of the adherence tracking system 100. For example, a regulatory agency may change its rules regarding the use of patient medical records. The administrator may then access the server 140 via the administrator workstation 149 and alter rules active in the modules 142-144 to reflect the changes in regulatory or interested third party rules.

For purposes of implementing the adherence tracking system 100, the primary point of contact with the patient is through a pharmacy 110. The pharmacist filling the prescription will have access to one of the pharmacy workstations 128 and may invoke the adherence tracking system 100 when he or she fills the patient's prescription. Alternatively, the adherence tracking system 100 may be invoked automatically for each new prescription entered or by a broader system, such as a medication management system. In some embodiments, the adherence tracking system 100 may be accessed by one or more additional computing devices (not shown) via the network 130 to generate and display reports regarding patient adherence for one or more patients.

Figure 2:
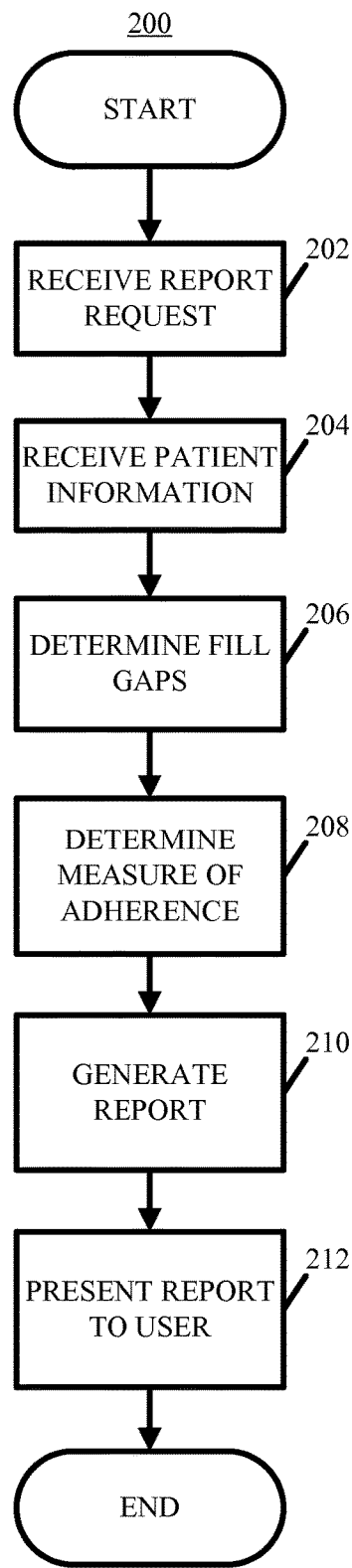
FIG. 2 illustrates an exemplary adherence tracking and reporting method for tracking adherence of a patient to a prescription medication regimen and generating a report regarding patient adherence.

FIG. 2 illustrates an exemplary adherence tracking and reporting method 200 for tracking adherence of a patient to a prescription medication regimen and generating a report regarding patient adherence. The method 200 begins at block 202 by receiving a request to generate a report. Information regarding the patient may then be obtained at block 204, including the patient's prescription history. This information may be used at block 206 to determine any fill gaps in the patient's prescription history where the patient did not have a sufficient supply of the prescription medication to meet the requirements of the prescription medication regimen. From the fill gaps, a measure of adherence may be determined at block 208. The measure of adherence may be used at block 210 to generate a report regarding patient adherence, which report may be presented to a user at block 212. In some embodiments, part or all of the method 200 may be implemented by the server 140 or by the pharmacy workstations 128 using information stored within the database 146 or additional databases accessible via the network 130.

The adherence tracking and reporting method 200 may be initiated upon a receipt at the server 140 of a request to generate a report regarding patient adherence at block 202. This request may be generated by a user interacting with the server 140 or the administrator workstation 149. For example, a user may operate an additional computing device (not shown) to generate and transmit a report request to the server 140 through the web server module 141 via the network 130. As another example, the report request may be generated automatically or in response to user input by any of the plurality of pharmacy workstations at any of the pharmacies 110 (e.g., in upon receipt of a new prescription for a patient, on a monthly basis, etc.). Additionally, or alternatively, the server 140 may generate a report request automatically upon the occurrence of specified conditions, such as the passage of time or receipt of information regarding a predetermined number of prescription fills of the prescription medication. The report request may be received at the server 140 from an interested third party via the network 130.

The report request received at block 202 may include information regarding the report, including metrics, requirements, filters, or criteria for the report. Such information may include a prescription medication or group of medications to include in the report, one or more patients to include in the report, one or more patient attributes for determining patients to include in the report (e.g., age, geographic location, home pharmacy location, number of pharmacy visits, other prescription or non-prescription medications taken, insurance coverage or insurer, adherence to other prescription medications, number of pharmacist consultations with the patient, etc.), one or more pharmacy locations to include in the report, one or more dispensing or consulting pharmacists to be included in the report, or one or more time periods to include in the report. The report request may further include information relating to adherence measures or metrics to be used in the report. For example, the report request may indicate that adherence should be reported using the proportion of days covered ("PDC"), which measures the number of days within a reference period during which the patient had access to a sufficient supply of the prescription medication, and the report request may further indicate that a patient may be determined to be adherent to the prescription medication regimen if the patient has a PDC score at or above 80%. As another example, the report request may indicate that adherence should be reported using the medication possession ratio ("MPR"), which measures adherence as the ratio of the total number of days' supply of the prescription medication received by the patient within the reference period to the total number of days within the reference period.

At block 204, the server 140 may receive information relating to one or more patients based upon the report request received at block 202. This patient information may include patient prescription histories and patient profiles for patients meeting the report criteria. The patient profile may be stored in the database 146 or in another database, which may be connected to the server 140 by the network 130. In some embodiments, the patient profile may include information regarding the prescription history of the patient. The server 140 may request data regarding the patient's medical history, including previously filled prescriptions. In one embodiment, the prescription history may be maintained by a third-party payor (e.g., an insurer, a pharmacy benefit manager, etc.) or other interested third party (e.g., a medical health plan, a healthcare provider, etc.). In some embodiments, receiving patient information at block 204 may include some or all of the aspects illustrated in the exemplary method of FIG. 3.

Figure 3:
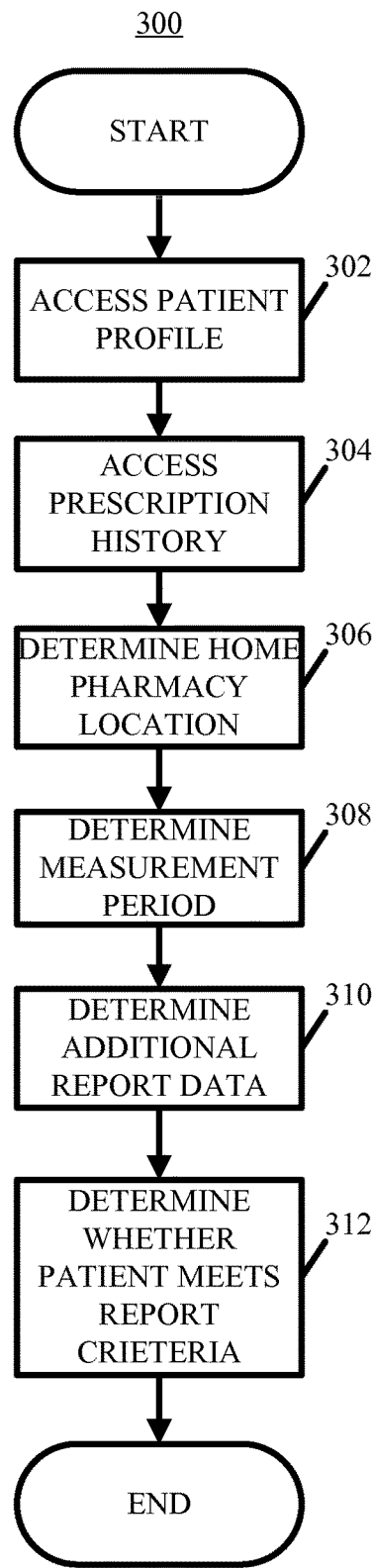
FIG. 3 illustrates an exemplary patient information determination and verification method for obtaining patient information and determining whether the patient information meets the criteria for the adherence report.

FIG. 3 illustrates an exemplary patient information determination and verification method 300 for obtaining patient information and determining whether the patient information meets the criteria for the adherence report. Although the exemplary method 300 is addressed to information relating to one patient, it should be understood that the method 300 may be applied serially or concurrently for each of a plurality of patients for which information is accessible. For example, each of the blocks 302-312 may be implemented by server 140 for each patient within a table of patients within database 146 (e.g., a table indicating all patients with a recorded fill of the prescription medication, etc.).

At block 302, the server 140 may access a patient profile, which may be stored in the database 146 or in another database communicatively connected to the server 140 via the network 130. In some embodiments, the patient profile may include one or more references to additional information regarding the patient stored in one or more additional databases (e.g., links to customer loyalty databases, links to customer reward point databases, links to employer-sponsored wellness initiatives or programs, etc.). The patient profile may include basic patient information, such as name, address, phone number, or insurance group number. In some embodiments, the patient profile may include information relating to customer loyalty programs, non-prescription medicine purchases, non-medical purchases, participation in third-party wellness programs, or other information regarding the patient.

At block 304, the server 140 may access the patient's prescription history. The prescription history may include, but is not limited to, data such as a list of the patient's prescriptions and, for each, the first fill date, one or more fill dates, one or more fill locations, the last fill date, a number of fills remaining, or other information related to the patient's prescriptions. In some embodiments, the server 140 may access the patient's prescription history by requesting via the network 130 information regarding the prescription history from one or more third-parties, such as insurers, health benefit managers, or government agencies. In some embodiments, the prescription history may be incorporated within the patient profile accessed at block 302, in which case block 304 may be absent from method 300.

At block 306, the server 140 may determine a home pharmacy location associated with the patient based upon the patient profile or the prescription history. The home pharmacy location may be a pharmacy at which the patient most frequently obtains one or more prescription medications. For example, the home pharmacy may be determined based upon the most recent prescription fills recorded in the patient's prescription history. As another example, the home pharmacy location may be determined based upon information within the patient profile, including one or more of the following: a mailing address of the patient, a telephone number of the patient, an insurance policy provider of the patient, a customer account of the patient, or the prescription history of the patient. The home pharmacy location may also be determined based upon an estimate or prediction of the location of future prescription fills for the patient. Determining a home pharmacy location may be particularly useful for report generation where a patient obtains prescription medication fills from more than one pharmacy location. For example, a patient may routinely obtain a prescription medication at a pharmacy location near their home, but may nonetheless occasionally have the same or another prescription filled at a pharmacy location near their place of business. In some instances, the server 140 may be unable to determine one home pharmacy for the patient. In some embodiments, therefore, the server 140 may determine a plurality of home pharmacy locations, which may be associated with different prescription medications or different time periods (e.g., when a patient moves or lives in multiple locations throughout the year). In other embodiments, the home pharmacy location may be left undetermined if insufficient information exists.

At block 308, the server 140 may determine a measurement period for determining measures of adherence of the patient to the prescription medication. Although the report request may set a time period for determination of adherence or minimum or maximum lengths of patient use of the prescription medication for inclusion in the report, the determination of a measurement period at block 308 may include information regarding a patient's first fill of one or more prescriptions or discontinuation of use of a prescription medication by a patient. Where a patient's prescription history indicates an extended fill gap of a predetermined length (e.g., six months, twelve months, etc.) between periods of more frequent fills, the measurement period may ignore the fills of the prescription before the extended fill gap and use the first fill following the extended fill gap as the beginning of the measurement period. The first fill within the determined measurement period may be later used in generating the adherence report. In some embodiments, determination of the measurement period may be based upon a therapeutic class or group of prescription medications, rather than one prescription medication. Additionally, or alternatively, information regarding non-prescription medications may be included in the determination of the measurement period.

At block 310, the server 140 may determine additional information regarding the patient to be included in the adherence report. The additional report data may include information regarding one or more of the following: patients, pharmacies, pharmacy locations, non-prescription medication purchases, non-medical purchases, pharmacists or physician consultations, changes in prescription medication or dosage, changes between classes or groups of medications, or other information from the patient profile or prescription history. In some embodiments, the additional report information may include information from one or more additional data sources not related to the patient profile or prescription history (e.g., gross pharmacy location revenues, total prescriptions filled at a pharmacy location, services or products offered at a pharmacy location, etc.). In some embodiments, the additional information may be determined or received from one or more third-party sources communicatively connected to the server 140 via the network 130.

At block 312, the server 140 may determine whether the accessed or determined patient information meets the criteria for the adherence report. The report criteria may be received with the report request, as discussed above, or the report criteria may be automatically generated or accessed from a predetermined set of criteria. For example, a periodic report may be generated on a monthly basis that includes only patients who received one or more fills of the prescription medication within the previous year. As another example, a report may be requested for one or more of the plurality of pharmacies 110 that includes information only for patients for whom those pharmacies 110 are home pharmacy locations. Inclusion or exclusion of the patient's information may further depend upon the prescribed medication, the dosage of the prescription medicine, the therapeutic class of the medication, the type of chronic illness or condition for which the medication is prescribed, the duration of the prescription, the patient's history with the prescribed medication or class of medications, the patient's history of adherence to unrelated medications, the patient's history of prior consultations regarding non-adherence to the prescribed medication or other medications, or other events in the patient's medical history where such events are known. Where the report is generated at the request of an interested third party, the determination of whether the patient meets the report criteria may include a determination of whether the patient information meets one or more criteria specified by the interested third party.

Returning to FIG. 2, at block 206, the server 140 may determine any fill gaps in the patient's prescription history where the patient had possession of an insufficient supply of the prescription medication to meet the requirements of the prescription medication regimen. The fill gaps may be determined based upon the prescription regimen information (e.g., doses per day, duration of course of treatment, etc.) and patient prescription history (e.g., dates of prescription fills, number of doses of each fill, etc.). The server 140 may determine the number of days of the prescription medication each prescription fill supplied, while maintaining a measure of the total supply of the prescription medication available to the patient for each day during the measurement period. Where the measure of the total supply of the prescription medication available to the patient is less than one day, the server 140 may include those days (or parts thereof) in a fill gap. In some embodiments, the measure of the total supply of the prescription medication may include one or more additional prescription medications (e.g., other prescription medications within the same therapeutic class that may be substituted for the prescription medication).

At block 208, the server 140 may use the determined fill gaps to determine a measure of adherence for each patient to be included in the adherence report. In some embodiments, this may be determined by subtracting the days in all the fill gaps from the total days from the first fill of the prescription medication within the measurement period to the end of the measurement period. In some embodiments, the end of the measurement period may be coincident with the date on which the report is generated. In other embodiments, the measurement period may include specified start and end dates. Various measures of adherence may be determined at block 208, such as PDC or MPR, days without the prescription medication, number of fill gaps longer than a predetermined length, or any other appropriate metric for measuring adherence of a patient to a prescription medication regimen.

Figure 4:
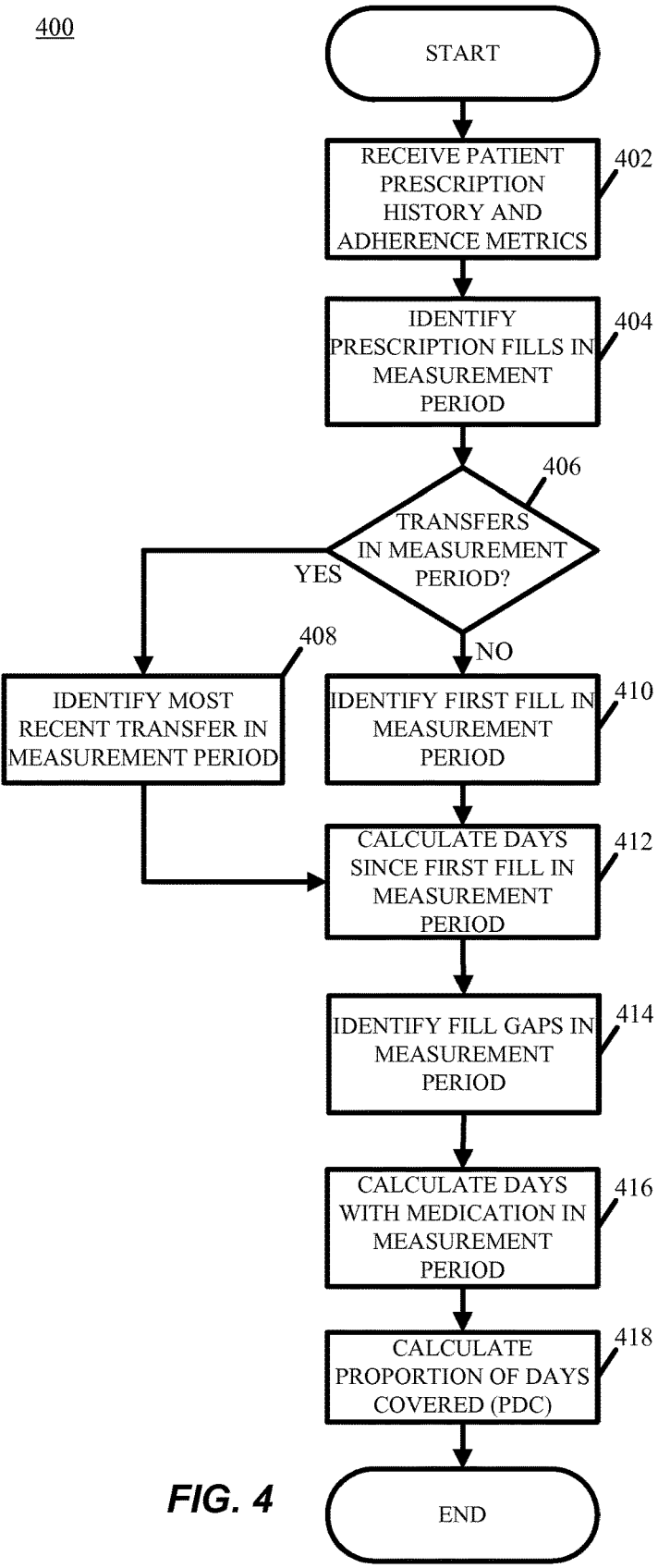
FIG. 4 illustrates an exemplary adherence determination method for determining a measure of adherence of a patient to a prescription medication regimen.

FIG. 4 illustrates an exemplary adherence determination method 400 for determining a measure of adherence of a patient to a prescription medication regimen. The measure of adherence determined in exemplary method 400 is a PDC metric, but other measures of adherence may be used in other embodiments. Although the exemplary method 400 is addressed to information relating to one patient, it should be understood that the method 400 may be applied serially or concurrently for each of a plurality of patients for which information may be included in the adherence report. For example, each of the blocks 402-418 may be implemented by server 140 for each patient within a set of patients meeting the report criteria, as previously discussed. In some embodiments, the method 400 may be implemented for each of a broader set of patients to determine a measure of adherence for each, which measure of adherence may be used as one of the report criteria.

At block 402, the server 140 may receive the patient prescription history and adherence metric information discussed above. The adherence metrics may include information regarding the measure of adherence, and the prescription history may include information regarding the prescription medication regimen. Using the prescription history information, at block 404, the server 140 may then identify any fills or refills of the prescription medication within the measurement period using the processor 162. In some embodiments, the identified fills or refills may include fills or refills of other prescription medications in a therapeutic class or group of prescription medications including the prescription medication. A therapeutic class may define a group of medications or a level within a hierarchical medicine classification scheme that have similar properties to the prescription medication. For example, a therapeutic class of a prescription for the branded medication Lipitor® may be the Medi-Span® Generic Product Identifier level 6 (GPI-6) therapeutic class of statins. After identifying all fills or refills of the prescription medication or related prescription medications within the therapeutic class, the server 140 may determine whether any of the fills or refills are transfer prescription fills at block 406. A transfer prescription fill may occur where a prescription is transferred from another pharmacy not within the pharmacies 110, such as may happen when a patient fills a prescription at an unaffiliated pharmacy and then transfers the prescription to a pharmacy 110 to obtain a fill. If one or more transfer prescription fills is identified at block 406, then the most recent transfer prescription fill may be identified at block 408. If no transfer prescription fills are identified within the measurement period at block 406, then the first fill or refill within the measurement period is identified at block 410. The first fill or refill identified at block 410 or the most recent transfer prescription fill identified at block 408 may be used as the start date for calculating the PDC.

At block 412, the server may determine with the processor 162 the number of days that have passed since the first fill or refill identified at block 410 or the most recent transfer prescription fill identified at block 408. For example, the prescription fills or refills identified in block 404 may include a first fill at an unaffiliated pharmacy (not shown) ninety days before the end date of the measurement period, a transfer fill at a pharmacy 110 sixty days before the end date of the measurement period, and a refill at pharmacy 110 twenty-seven days before the end date of the measurement period. In this example, block 412 would calculate the number of days that have passed since the most recent transfer prescription fill identified at block 408 as sixty days. The first fill is ignored because it precedes the most recent transfer prescription fill. At block 414, the server 140 may identify any fill gaps within the measurement period based upon prescription history. In the preceding example, one fill gap of three days would be identified by the processor 162, beginning thirty days before the end date of the measurement period (upon exhaustion of the thirty-day supply from the transfer fill) and ending twenty-seven days before the end date of the measurement period (upon receipt of the next thirty-day supply by the patient). At block 416, the server 140 may then calculate the days the patient had a sufficient supply of the prescription medication by subtracting the length of all fill gaps identified in block 414 from the number of days since the first fill within the measurement period calculated at block 412. Continuing with the same example, the processor 162 would calculate the number of days with the prescription medication as fifty-seven, comprising thirty days from the transfer fill and twenty-seven days from the refill; the three days of the fill gap are excluded. At block 418, the server 140 may then calculate the PDC metric as the number of days with the medication calculated at block 416 as a proportion of the number of days since the first fill in the measurement period calculated at block 412. In the example, the PDC would be calculated as fifty-seven days with medication divided by sixty days since the transfer fill, yielding a PDC of 0.95. In some embodiments, the PDC may be described in percentage terms. For the example above, the PDC may thus be stated as 95%.

In some embodiments, one or more fills within the measurement period may be partial fills, for which the supply of the prescription medication dispensed to the patient is less than the prescription amount. This may occur when the supply of the prescription medication available at a pharmacy 110 is insufficient to fully fill or refill the prescription. In such cases, a second partial fill may occur to fill the remainder of the prescription amount at a later date. Where one or more of the fills within the measurement period is a partial fill, the server 140 may determine the number of days the patient had a sufficient supply of medication in hand when identifying fill gaps at block 414 by considering only the supply actually received by the patient at the time of each partial fill and the date the prescription was partially filled.

Returning to FIG. 2, at block 210, the server 140 may generate the report based upon the measure of adherence determined in block 208. The report may include information regarding adherence for a plurality of patients based upon the report criteria and other requirements received in block 202 or otherwise determined. The report may further include additional report information, such as that discussed above with respect to block 310. For example, the report may include average measures of adherence for each of a plurality of prescription medications within a group of related prescription medications of the same therapeutic class. Alternatively, the report may include a comparison of percentages of patients with adherence below a threshold level for one or more prescription medications across a plurality of pharmacy locations. As yet a further example, the report may include information regarding correlations between non-prescription medication purchases and adherence rates for the prescription medication, which may indicate side effects of the prescription medication or patient substitutions of non-prescription medication for the prescription medication.

In some embodiments, the report may include instructions or recommendations indicating whether new-to-therapy information should be presented to a patient upon starting a new prescription medication regimen. The new-to-therapy information may include information regarding the prescription medication, proper usage of the prescription medication, potential adverse effects of the prescription medication, warning regarding drug interactions with other prescription or non-prescription medications, or similar information. In some embodiments, the determination of whether to include new-to-therapy instructions or recommendations in the report may include aggregate information regarding adherence of a plurality of patients, such as average adherence rates for the prescription medication, alone or in combination with other medications. Such aggregate or average adherence information for a plurality of patients may include a measure of adherence with respect to one or more of the following: the prescription medication, a dosage of the prescription medicine, a therapeutic class including the prescription medication, a pharmacy location associated with the new prescription fill, a home pharmacy location associated with the patient, or demographic information regarding the patient.

In some embodiments, patient adherence to other prescription medications in the past may be used to determine whether to initiate an introductory contact or consultation to present new-to-therapy information to the patient. In such embodiments, an appropriate instruction or recommendation may be included within the report generated at block 210. For example, a patient returning to therapy with a prescription medication after an extended fill gap of several years who had a high measure of adherence until the beginning of the extended fill gap may not need the new-to-therapy information, which may be reflected in the information within the generated report.

In further embodiments, information regarding one or more purchases associated with the patient at one or more pharmacy locations may be used to determine whether to include an instruction or recommendation to hold a patient consultation in the generated report. For example, a low patient adherence and frequent purchases of antacids by the patient may indicate a side effect that a pharmacist may be better able to address through a consultation with the patient. In some embodiments, the report generated at block 210 may include instructions that may be implemented by the server 140 or other computer system to further generate automated messages or communications.

At block 212, the server 140 may present or cause to be presented the report or information relating to the report to a user. The report may be displayed using an electronic display or presented in a physical embodiment, such as a printed copy. The information displayed may include the full report or a summary thereof. In some embodiments where the report includes instructions that may be implemented by the server 140 or other computer system, the presentation may consist of an indication that the report has been run. In some embodiments, the report may not be presented to a user.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in exemplary configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (code embodied on a non-transitory, tangible machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as exemplary only and does not describe every possible embodiment, as describing every possible embodiment would be impractical, if not impossible. One could implement numerous alternate embodiments, using either current technology or technology developed after the filing date of this application.

What is claimed is:

1. A computer-implemented method for tracking adherence of a patient to a treatment regimen including a prescription medication, comprising:

collecting, by a processor, transaction data regarding products or services provided to the patient at one or more pharmacies;

generating, by a processor, a patient profile associated with the patient based upon the transaction data, wherein the patient profile includes data comprising a prescription history of the patient and non-prescription product purchases associated with the patient;

receiving, at a processor, a request from the patient to fill or refill a prescription;

automatically generating, by a processor and in response to the request from the patient to fill or refill the prescription, a triggering event command to generate a report associated with adherence of the patient to the treatment regimen;

accessing, by a processor and in response to the triggering event, the patient profile associated with the patient;

receiving, at a processor, information regarding the prescription history of the patient from the patient profile, wherein the prescription history includes a first instance in which the patient has received the prescription medication and one or more subsequent instances in which the patient has received the prescription medication following the first instance;

determining, by a processor, one or more fill gaps between any of the first instance and the one or more subsequent instances based upon the prescription history in response to the triggering event command, wherein each fill gap is a period of time during which the patient had an insufficient supply of the prescription medication for the treatment regimen;

calculating, by a processor, a value of a measure of adherence of the patient to the treatment regimen based on the one or more fill gaps;

receiving, at a processor, additional information indicating the non-prescription medical product purchases associated with the patient from the patient profile;

identifying, by a processor, a non-prescription medical product purchase of a non-prescribed medical product known to be associated with treatment of side effects of the prescription medication from the additional information;

generating, by a processor, a notification to hold a consultation with the patient regarding the prescription medication in response to identifying the non-prescription medical product purchase and the value of the measure of adherence of the patient to the treatment regimen;

generating, by a processor, the report based at least in part upon the calculated measure of adherence, wherein the report includes the notification to hold the consultation; and presenting, by a display, the report to a user.

2. The computer-implemented method of claim 1, further comprising:

receiving, at a processor, an indication of a new prescription to fill for the patient; and determining, by a processor, whether to include an instruction to provide new-to-therapy information to the patient in the report based upon the prescription history of the patient and the measure of adherence of the patient to the treatment regimen including the prescription medication.

3. The computer-implemented method of claim 2, wherein:
the new prescription relates to a second prescription medication; and
the new-to-therapy information includes information regarding the second prescription medication and information regarding proper usage.

4. The computer-implemented method of claim 2, wherein determining whether to include the instruction in the report is further based upon information regarding the prescription medication, including at least one adherence metric for a plurality of patients and relating to one or more of the following: the prescription medication, a dosage of the prescription medicine, a dosage of the prescription medicine, a therapeutic class including the prescription medication, a pharmacy location associated with the new prescription fill, a home pharmacy location associated with the patient, or demographic information regarding the patient.

5. The computer-implemented method of claim 1, further comprising determining, by a processor, a home pharmacy location associated with the patient, wherein:
the home pharmacy location is one of a plurality of pharmacy locations at which the patient has received a fill of one or more prescription medications; and
the home pharmacy location is determined at least in part based upon one or more of the following: a mailing address of the patient, a telephone number of the patient, an insurance policy provider of the patient, a customer account of the patient, or the prescription history of the patient.

6. The computer-implemented method of claim 5, wherein the generated report includes information regarding the patient and a plurality of additional patients associated with the home pharmacy location.

7. The computer-implemented method of claim 1, wherein the additional information includes information regarding one or more locations associated with the non-prescription medical product purchases.

8. The method of claim 1, wherein:
the prescription history includes one or more of the first instance or subsequent instances in which the patient has received a second prescription medication in the same therapeutic class as the prescription medication; and
each fill gap is a period of time during which the patient had an insufficient supply of either the prescription medication or the second prescription medication according to the treatment regimen.

9. The method of claim 1, wherein the measure of adherence comprises at least one of a measure of a proportion of days covered by the prescription medication or a measure of a medication possession ratio, and wherein:
the proportion of days covered by the prescription medication comprises a proportion of a number of days in a measurement period for which the patient had a sufficient supply of the prescription medication according to the treatment regimen to a number of days in the measurement period;
the medication possession ratio comprises a ratio of a measure of days supplied by a cumulative total of all instances in which the patient received the prescription medication during the measurement period according to the treatment regimen to the number of days in the measurement period; and the measurement period is the shorter of (i) a period between the first instance and an end date for determining the measure of adherence and (ii) a period of predetermined length immediately preceding the end date for determining the measure of adherence.

10. A computer system for tracking adherence of a patient to a treatment regimen including a prescription medication, comprising:
one or more processors;
one or more databases;
a tangible program memory storing executable instructions that, when executed by the one or more processors, cause the computer system to:
collect transaction data regarding products or services provided to the patient at one or more pharmacies;
generate a patient profile associated with the patient based upon the transaction data, wherein the patient profile includes data comprising a prescription history of the patient and non-prescription product purchases associated with the patient;
receive a request from the patient to fill or refill a prescription;
automatically generate a triggering event command to generate a report associated with adherence of the patient to the treatment regimen in response to the request from the patient to fill or refill the prescription;
in response to the triggering event, access the patient profile associated with the patient;
receive information regarding the prescription history of the patient from the patient profile, wherein the prescription history includes a first instance in which the patient has received the prescription medication and one or more subsequent instances in which the patient has received the prescription medication following the first instance;
determine one or more fill gaps between any of the first instance and the one or more subsequent instances based upon the prescription history in response to the triggering event command, wherein each fill gap is a period of time during which the patient had an insufficient supply of the prescription medication for the treatment regimen;
calculate a value of a measure of adherence of the patient to the treatment regimen based on the one or more fill gaps;
receive additional information indicating the non-prescription medical product purchases associated with the patient from the patient profile;
identify a non-prescription medical product purchase of a non-prescribed medical product known to be associated with treatment of side effects of the prescription medication from the additional information;
generate a notification to hold a consultation with the patient regarding the prescription medication in response to identifying the non-prescription medical product purchase and the value of the measure of adherence of the patient to the treatment regimen;
generate a report based at least in part upon the calculated measure of adherence, wherein the report includes the notification to hold the consultation; and
cause the report to be presented to a user.

11. The computer system of claim 10, wherein the executable instructions, when executed by the one or more processors, further cause the computer system to:
receive an indication of a new prescription to fill for the patient; and determine whether to include an instruction to provide new-to-therapy information to the patient in the report based upon the prescription history of the patient and the measure of adherence of the patient to the treatment regimen including the prescription medication.

12. The computer system of claim 11, wherein:
the new prescription relates to a second prescription medication; and
the new-to-therapy information includes information regarding the second prescription medication and information regarding proper usage.

13. The computer system of claim 10, wherein the executable instructions, when executed by the one or more processors, further cause the computer system to determine a home pharmacy location associated with the patient, wherein:
the home pharmacy location is one of a plurality of pharmacy locations at which the patient has received a fill of one or more prescription medications; and
the home pharmacy location is determined at least in part based upon one or more of the following: a mailing address of the patient, a telephone number of the patient, an insurance policy provider of the patient, a customer account of the patient, or the prescription history of the patient.

14. The computer system of claim 13, wherein the generated report includes information regarding the patient and a plurality of additional patients associated with the home pharmacy location.

15. A tangible, non-transitory computer-readable medium storing instructions for tracking adherence of a patient to a treatment regimen including a prescription medication that, when executed by at least one processor of a computer system, cause the computer system to:
collect transaction data regarding products or services provided to the patient at one or more pharmacies;
generate a patient profile associated with the patient based upon the transaction data, wherein the patient profile includes data comprising a prescription history of the patient and non-prescription product purchases associated with the patient;
receive a request from the patient to fill or refill a prescription;
automatically generate a triggering event command to generate a report associated with adherence of the patient to the treatment regimen in response to the request from the patient to fill or refill the prescription;
in response to the triggering event, access the patient profile associated with the patient;
receive information regarding the prescription history of the patient from the patient profile, wherein the prescription history includes a first instance in which the patient has received the prescription medication and one or more subsequent instances in which the patient has received the prescription medication following the first instance;
determine one or more fill gaps between any of the first instance and the one or more subsequent instances based upon the prescription history in response to the triggering event command, wherein each fill gap is a period of time during which the patient had an insufficient supply of the prescription medication for the treatment regimen;
calculate a measure of adherence of the patient to the treatment regimen based on the one or more fill gaps;
receive additional information indicating the non-prescription medical product purchases associated with the patient from the patient profile;
identify a non-prescription medical product purchase of a non-prescribed medical product known to be associated with treatment of side effects of the prescription medication from the additional information;
generate a notification to hold a consultation with the patient regarding the prescription medication in response to identifying the non-prescription medical product purchase and the value of the measure of adherence of the patient to the treatment regimen;
generate a report based at least in part upon the calculated measure of adherence, wherein the report includes the notification to hold the consultation; and
cause the report to be presented to a user.

16. The tangible, non-transitory computer-readable medium of claim 15, further storing instructions that, when executed by at least one processor of a computer system, cause the computer system to:
receive an indication of a new prescription to fill for the patient; and
determine whether to include an instruction to provide new-to-therapy information to the patient in the report based upon the prescription history of the patient and the measure of adherence of the patient to the treatment regimen including the prescription medication.

17. The tangible, non-transitory computer-readable medium of claim 15, further storing instructions that, when executed by at least one processor of a computer system, cause the computer system to determine a home pharmacy location associated with the patient, wherein:
the home pharmacy location is one of a plurality of pharmacy locations at which the patient has received a fill of one or more prescription medications; and
the home pharmacy location is determined at least in part based upon one or more of the following: a mailing address of the patient, a telephone number of the patient, an insurance policy provider of the patient, a customer account of the patient, or the prescription history of the patient.

18. The tangible, non-transitory computer-readable medium of claim 15, wherein the additional information includes information regarding one or more locations associated with the non-prescription medical product purchases.

* * * * *